US008256898B2

(12) United States Patent
Gratton et al.

(10) Patent No.: US 8,256,898 B2
(45) Date of Patent: Sep. 4, 2012

(54) METHOD AND DEVICE FOR TEAR FILM ANALYSIS

(75) Inventors: Enrico Gratton, San Clemente, CA (US); Kaveh Azartash, Laguna Hills, CA (US); Luisa Marsili, Frascati (IT)

(73) Assignee: The Regents of the University of California, Oakland, CA (US)

( * ) Notice: Subject to any disclaimer, the term of this patent is extended or adjusted under 35 U.S.C. 154(b) by 170 days.

(21) Appl. No.: 12/813,423

(22) Filed: Jun. 10, 2010

(65) Prior Publication Data
US 2010/0315591 A1 Dec. 16, 2010

Related U.S. Application Data

(60) Provisional application No. 61/186,767, filed on Jun. 12, 2009.

(51) Int. Cl.
*A61B 3/14* (2006.01)
*A61B 3/10* (2006.01)
(52) U.S. Cl. .................. 351/206; 351/221; 351/205
(58) Field of Classification Search ........... 351/200–246
See application file for complete search history.

(56) References Cited

U.S. PATENT DOCUMENTS 5,886,767 A * 3/1999 Snook ........................... 351/212
2008/0319323 A1* 12/2008 Gravely et al. ............... 600/476

OTHER PUBLICATIONS

King-Smith, P. Ewen et al., Mini-Review: The Thickness of the Tear Film, Current Eye Research, 2004, vol. 29, Nos. 4-5, pp. 357-368.
King-Smith, P. Ewen et al., The Thickness of the Human Precorneal Tear Film: Evidence from Reflection Spectra, IOVS, Oct. 2000, vol. 41, No. 11, pp. 3348-3359.
Lieznerski, Tomasz J. et al., Analysis of Shearing Interferograms of Tear Film Using Fast Fourier Transforms, Journal of Biomedical Optics, 3(1), 32-37 (Jan. 1998).
Montes-Mico, Robert et al., Dynamic Changes in the Tear Film in Dry Eyes, IOVS, May 2005, vol. 46, No. 5, pp. 1615-1619.
Nemeth, Janos et al., High-Speed Videotopographic Measurement of Tear Film Build-up Time, IOVS, Jun. 2005, vol. 43, No. 6, pp. 1783-1790.
Nichols, Jason J. et al., Thickness of the Pre- and Post-Contact Lens Tear Film Measured in Vivo by Interferometry, IOVS, Jan. 2003, vol. 44, No. 1, pp. 68-77.

(Continued)

*Primary Examiner* — Mohammed Hasan
(74) *Attorney, Agent, or Firm* — Vista IP Law Group LLP

(57) ABSTRACT

Tear film stability has an important role in the quality of vision. A system and method for performing Fluctuation Analysis of Spatial Image Correlation (FASIC) provides for a non-invasive system and method for evaluating the dynamics of the tear film surface using spatial autocorrelation analysis. With FASIC, a series of images are obtained using illumination and a camera. The spatial autocorrelation is calculated for image frames produced by the camera. A sinusoidal background appears in this correlation together with other features. The changes in the sinusoidal background of the spatial autocorrelation is extracted and monitored over time. The spatial period of this sinusoidal background correlates with the thickness of the tear film. In this regard, one is able to derive the tear film thickness from the period of this sinusoidal background.

20 Claims, 14 Drawing Sheets

OTHER PUBLICATIONS

Prydal, Jeremy I. et al., Study of Precorneal Tear Film Thickness and Structure by Interferometry and Confocal Microscopy, IOVS, vol. 33, No. 6, May 1992, pp. 1996-2005.

Szczena, Dorota H. et al., An Interferometric Method for the Dynamic Evaluation of the Tear Film, Acta Ophthalmol. Scand., 2007:85:202-208.

Szczesna, Dorota H. et al., Numerical Analysis of Interferograms for Evaluation of Tear Film Build-up Time, Ophthal. Physiol. Opt. 2009, 29: 211-218.

Wang, J. et al., Precorneal and Pre- and Postlens Tear Film Thickness Measured Indirectly with Optical Coherence Tomography, IOVS, Jun. 2005, vol. 44, No. 6, pp. 2524-2528.

* cited by examiner

METHOD AND DEVICE FOR TEAR FILM ANALYSIS

RELATED APPLICATION

This application claims priority to U.S. Provisional Patent Application No. 61/186,767 filed on Jun. 12, 2009. U.S. Patent Application No. 61/186,767 is incorporated by reference as if set forth fully herein. Priority is claimed pursuant to 35 U.S.C. §119 and any other applicable statute.

STATEMENT REGARDING FEDERALLY SPONSORED RESEARCH OR DEVELOPMENT

This invention was made with Government support under Grant No. RR003155, awarded by the National Institutes of Health. The Government has certain rights to this invention.

FIELD OF THE INVENTION

The field of the invention generally relates to non-invasive methods and devices used to analyze the ocular tear film. More specifically, the field of the invention pertains to devices and methods that rely on or use the spatial autocorrelation of a two dimensional laser speckle and interference pattern to quantify the tear film thickness and/or its morphological features.

BACKGROUND OF THE INVENTION

Tears are formed by tiny glands that surround the eye. The tear film is comprised generally of three layers including oil, water, and mucous. The lower mucous layer generally serves to anchor the tear film to the eye. The middle layer is comprised of water while the upper oil layer seals the tear film and prevents or mitigates evaporation. Dry eye syndrome (DES), also known as Keratoconjunctivitis-sicca, is a disorder of the tear film due to tear deficiency or excessive tear evaporation which causes damage to the interpalpebral ocular surface and is associated with symptoms of ocular discomfort. Tear film instability may cause alteration in volume, composition, or distribution, of the tear film, thus assessing the dynamics of tear film is very important in addressing the DES.

The human tear film is the outermost layer in the eye. As explained above, it is composed of an outer oily or lipid layer over a mixture of aqueous and mucus layers. The tear film lubricates the cornea of the eye and keeps the front of the eyeball moist and clean. The tear film is also the first refractive medium of the eye and acts as shield to protect the eye from foreign objects and bacteria. Therefore, tear film is an important factor in evaluating the quality of vision, both optically and physiologically.

Analyzing the tear film quality and dynamics are complex tasks. The most commonly used diagnostic methods, such as the Schirmer test, Rose Bengal, and fluorescein staining, are invasive and can be uncomfortable for the patient. These techniques are subjective and do not provide quantitative information. They also exhibit high variability. Amongst the non-invasive techniques, high-speed videotopography has been applied to measure the tear film build-up time. Videotopography is described, for example, in J. Nemeth et al., *High-Speed Videotopographic Measurement of Tear Film Build-up Time*, Invest. Opthalmol. Vis. Sci. 43(6), 1783-1790 (2002).

Another technology, wavefront aberrometry has been used to quantify the tear break-up time (TBUT). This technique is described, for instance, in R. Montes-Mico et al., *Dynamic Changes in the Tear Film in Dry Eyes*, Invest. Opthalmol. Vis. Sci. 46(5), 1615-1619 (2005). Interferometry has also been applied in measuring the thickness of the tear film. There are two different interferometry techniques that have been proposed and applied in the opthalmology research community. King-Smith et al. were amongst the pioneers in applying interferometry to tear film studies. Their approach was to analyze the reflectance spectra from the tear film using visible and near-infrared light source. King-Smith et al. analyzed the modulation and phase of the oscillations in the spectra. King-Smith et al. were able to quantify the thickness of the pre-corneal tear film and for the first time obtain a value of 3 μm. The King-Smith et al. techniques are discussed, for example, in King-Smith et al., *The thickness of the tear film*, Current Eye Research, pp. 357-368, Informa Healthcare, London (2004); King-Smith et al., *The Thickness of the Human Pre-corneal Tear Film: Evidence from Reflection Spectra*, Invest. Opthalmol. Vis. Sci. 41(11), 3348-3359 (2000); King-Smith et al., *Thickness of the Pre- and Post-Contact Lens Tear Film Measured In Vivo by Interferometry*, Invest. Opthalmol. Vis. Sci. 44(1), 68-77 (2003); and King-Smith et al., *Three Interferometric Methods for Measuring the Thickness of Layers of the Tear Film*, Optometry & Vision Science 76(1), 19-32, (1999).

Licznerski et al. modified the lateral shearing interferometry method and initiated a cascade of applications by scientists in the field. The Licznerski et al. is described, for example, in T. J. Licznerski et al., *Analysis of Shearing Interferograms of Tear Film Using Fast Fourier Transforms*, Journal of Biomedical Optics 3(1), 32-37 (1998). This method was mainly applied by Szczesna et al. to evaluate the dynamics of the tear film. Szczesna et al. were able to assess the stability of the tear film on the cornea and on contact lenses. In this method, interference patterns undergo a fast Fourier transformation to analyze the changes in the orientation of the fringes in interferograms. Quantitative information can be revealed from the spectra in the fast Fourier transformed images as described in Szczesna et al., *Numerical analysis of interferograms for evaluation of tear film build-up time*, Ophthalmic and Physiological Optics 29(3), 211-218 (2009) and Szczesna et al., *An interferometric method for the dynamic evaluation of the tear film*, Acta Opthalmologica Scandinavica 85(2), 202-208 (2007). However, these techniques have not been applied routinely yet.

Optical coherence tomography (OCT) has also been applied to tear film measurements. OCT is a non-invasive cross-sectional imaging methodology in biomedical applications. Low coherence light source is applied in the OCT systems to obtain a two dimensional image that could reveal optical characteristics of the specimen. However, OCT generally does not have the resolution in the axial direction to directly measure the tear film. Wang et al. has, however, used a commercial OCT to indirectly measure the thickness of the normal pre-corneal tear film. This is described in Wang et al., *Precorneal and Pre- and Post lens Tear Film Thickness Measured Indirectly with Optical Coherence Tomography*, Invest. Opthalmol. Vis. Sci. 44(6), 2524-2528 (2003).

SUMMARY

In one aspect of the invention, a non-invasive method for evaluating the thickness and spatial features of the ocular tear film is accomplished using Fluctuation Analysis of Spatial Image Correlation (FASIC) by applying the basis of spatial autocorrelation technique. The system and method are robust, portable, low-cost and easy to align. This technique allows for the quantitative assessment of the spatial fluctuations in a series of images. The spatial fluctuations can be translated into thickness information using a mathematical model. In addition, by calculating spatial autocorrelation in the raw camera images, the microscopic features of the profile of tear film can thus be obtained.

In another aspect of the invention, a method of determining the thickness of a tear film of a subject includes irradiating an eye with a light source and capturing a speckle and interference pattern produced by the irradiated eye with a camera, the camera capturing the speckle and interference patterns in a plurality of frames. The light source could be a laser, a combination of lasers with multiple wavelengths, LED (or multiple LEDs), or a tungsten light. A spatial autocorrelation of the raw camera image is then calculated for the plurality of frames and the primary Gaussian component is removed or subtracted from the spatial autocorrelation so as to leave sinusoidal residues. The sinusoidal residues are then subject to horizontal and vertical fitting with a periodic function, the periodic function associated with an interference term. Finally, the thickness is determined based at least in part on the interference term, which is related to the frequency of the periodic pattern that is seen in the raw camera image.

In another aspect of the invention, a system for determining the thickness of a tear film of a subject includes a source of radiation, a camera configured to capture a speckle and interference pattern produced by the irradiated eye in a plurality of frames, at least one microprocessor configured to calculate a spatial autocorrelation of the raw camera image for the plurality of frames, the at least one microprocessor further configured to remove the primary Gaussian component from the spatial autocorrelation so as leave sinusoidal residues and subjecting the sinusoidal residues to horizontal and vertical fitting with a periodic function, the periodic function associated with an interference term, the at least one microprocessor further configured for determining the thickness based at least in part on the interference term. The at least one microprocessor may include a one or more dedicated processors or the microprocessor(s) may be included in a separate personal computer or the like that is used to analyze and process image data from the camera.

BRIEF DESCRIPTION OF THE DRAWINGS

FIG. 2A is the raw camera image. FIG. 2B is the fast Fourier transformed image. FIG. 2C is the complex conjugate image. FIG. 2D is the product of (B) and (C) which produces the spatial autocorrelation function.

DETAILED DESCRIPTION OF THE INVENTION

Figure 1A:
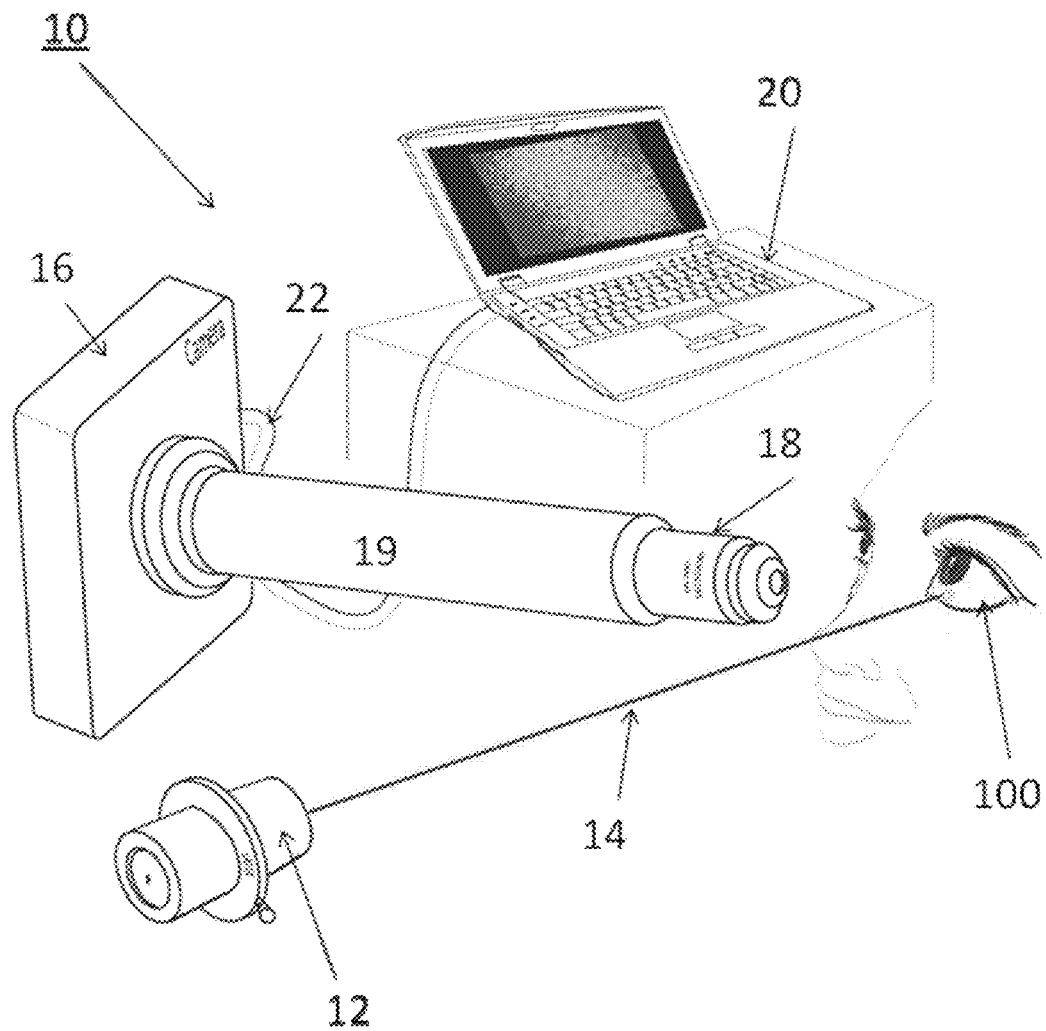
FIG. 1A illustrates a schematic representation of an imaging system according to one embodiment. The camera assembly is distanced at the focal length of the object.

A schematic of the imaging system 10 is illustrated in FIG. 1A. The imaging system 10 generally includes an illumination source 12 that is used to direct radiation 14 onto the surface of the eye 100. The illumination source 12 may include a laser or light emitting diode (LED). The laser may have a narrow wavelength range or, alternatively, the laser may include a white or broadband wavelength. In the later case, the broader wavelength range can provide additional information on the components and physical features of the tear film. In yet another alternative, two or more lasers (or LEDs) may be used with each laser (or LED) having a different wavelength. Multiple wavelengths would provide additional information on the components of the tear film.

As another alternative, a monochromatic LED may be used. The LED as a light source would remove the speckles. With a monochromatic LED, one would only need to analyze the interference pattern. In still another alternative, a broadband light source such as a tungsten light source (e.g., white light) source may be another option for the illumination source 12 that produces a broadband source of light over a wider range of wavelengths.

While FIG. 1A illustrates radiation 14 passing directly from the illumination source 12 to the eye 100, an optional filter such as, for example, a neutral density filter (not shown) may be interposed between the illumination source 12 and the eye 100. The filter may be used to select (or deselect) appropriate wavelengths or to decrease light intensity. One example of a filter that may be used with the system 10 is an acousto-optical tunable filter (AOTF). This type of filter would permit wavelength selection.

Still referring to FIG. 1A, the imaging system 10 includes a camera 16 that is configured to capture radiation reflected and/or scattered from the eye 100. The camera 16 is preferably a digital-based camera that is capable of capturing a plurality of image frames over a period of time. Such cameras 16 may include cameras 16 that include a charge-coupled device (CCD) or complimentary metal-oxide semiconductor (CMOS) sensor or chip.

One or more lenses 18 may optionally be used to focus reflected light into the camera 16. In addition, as seen in FIG. 1A, an optional extender tube 19 may be used in conjunction with the lens(es) 18 to maintain the focus onto the imaging sensor of the camera 16.

Still referring to FIG. 1A, the system 10 includes a computer 20 that is used for data acquisition and analysis. A cable 22 connects the camera 16 to the computer 20 to transfer image frame date from the camera 16 to the computer 20. The computer 20 illustrated in FIG. 1A is a personal laptop although other computers may be used. The computer 20 typically includes a data storage device onto which frame data can be stored. The computer 20 includes one or more processors that are used to process and analyze the imaging data. Software is loaded onto the computer 20 and can be used to implement the calculations described in more detail herein.

FIG. 1A illustrates one exemplary embodiment of an imaging system 10. In this embodiment, the illumination source 12 is a 635 nm class II laser (0.8 mW power) used as a monochromatic coherent light source. The wavelength and power of this illumination source 12 are in compliance with ANSII-2007 standards for eye safety. This laser can be used for measurements of tear film in a human eye 100. The laser beam is shined directly onto the eye 100 and onto the inferior cornea. The incident angle was approximately 10 degrees although it should be understood that other incident angles may be used. The camera angle was slightly greater than the incident angle. The diameter of the illuminated area on the eye 100 is approximately 1 mm-2 mm although the particular diameter is influenced by the particular light source and may be larger or smaller. The scattering caused by particles on the ocular surface of the eye 100 and reflection from the tear film layer is captured by a CMOS camera 16 (PL-A662-KIT, Pixelink, Ottawa, ON K1G 6C2). When the coherent light source (e.g., laser) hits a non-smooth surface it creates speckles and an interference pattern. The speckle pattern is produced by mutual constructive and deconstructive interference of a set of wavefronts. This speckle and interference pattern is captured by the CMOS camera 16.

The objective lens 18 in FIG. 1A (Mitutoyo Compact CF 1X Objective, Edmund Optics, N.J., USA) is connected to the CMOS camera 16 through an extender tube 19 to maintain the correct focus. The objective lens 18 may have a diameter of 8 mm and the distance from the cornea of the eye 100 may be around 68 mm, given an acceptance angle of approximately 0.12 rad although other dimensions and distances may be used. The extender tube 19 may have a number of lengths but a length of around 15 cm may be typical. An optional polarizer filter (not shown) could be added to the optical path to select reflections from the surface or from scattered light from deeper layers. In addition, other objective lenses 18 and/or extender tubes 19 could be used as part of the system 10. A sequence of 256×256 pixel images (e.g., image frames) are streamed to a computer 20 through a FireWire cable 22. Data acquisition software loaded onto the computer 20 is used to acquire image data. An example of commercially available data acquisition software includes SimFCS®, available for download at http://www.lfd.uci.edu/globals/. The exposure time of the camera 16 was set at 1 ms in order to acquire the images at approximately 300 frames per second (fps). This high frame rate enables the capture of every fluctuation occurring in the tear film to about maximum of about 150 Hz. For each experiment about 2000 to 3000 frames were obtained. Therefore, the overall data acquisition time would not exceed 6 to 8 seconds. Fewer number of frames could also be obtained to expedite the calculation process. In other experiments involving human subjects, around 1000 frames were collected for a total acquisition time of around 4 seconds. If desired, this time can be shortened by acquiring fewer frames (or lengthened by adding more frames).

Using the imaging system 10 of FIG. 1A, a sequence of laser speckled/interference image frames is sent from the camera 16 to the computer 20. By analyzing the spatial fluctuations on a pixel-by-pixel basis in a sequence of time-integrated laser speckle images, the depth profile information of the tear layer can be obtained as well as spatial features of the tear film. The method applies the unique characteristics of spatial autocorrelation analysis to obtain the quantitative dynamics of tear film. By using spatial autocorrelation analysis of speckle and interference images, the thickness of tear film can be obtained.

Figure 1B:
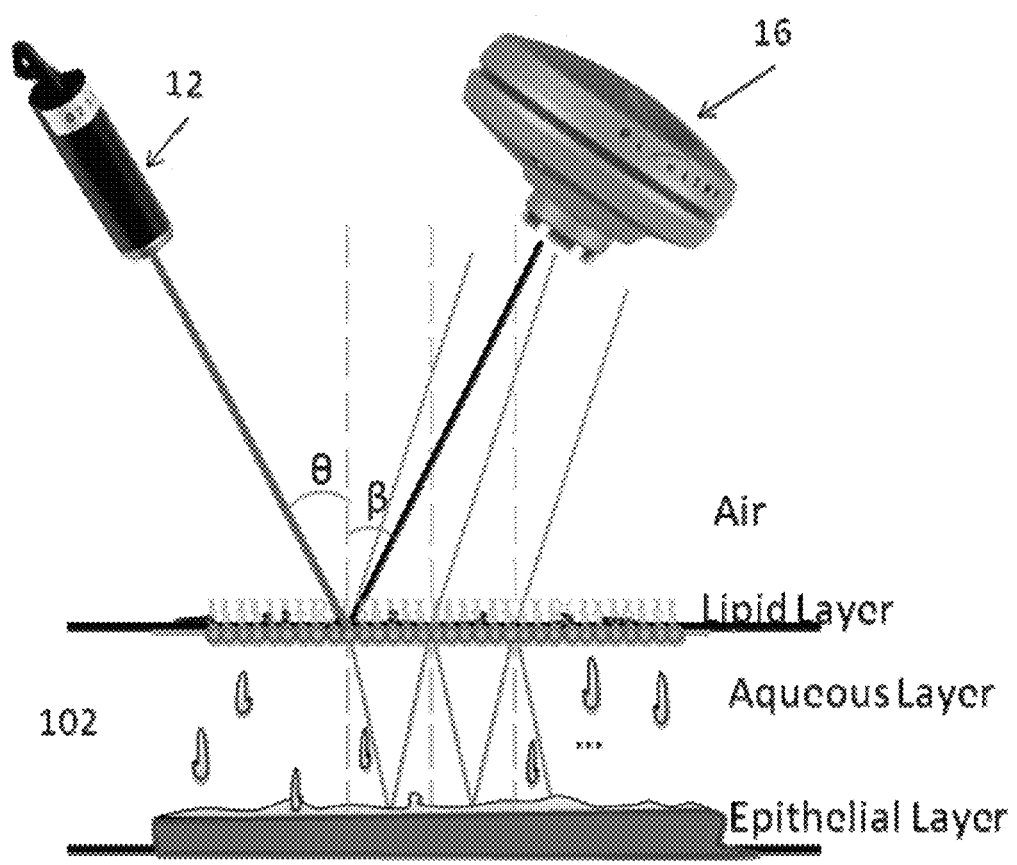
FIG. 1B illustrates the physical principles behind the formation of the interference pattern available in the raw camera image.

FIG. 1B illustrates the physical principles behind the formation of the interference pattern available in the raw camera image. As illustrated in FIG. 1B, the illumination source 12 is a low power 635 nm laser beam that illuminates the ocular surface at an angle θ. The scattered light from the surface forms constructive and deconstructive interference patterns with the reflected light from the lower layer of the tear film 102. The camera assembly, positioned at an angle β, captures these patterns.

The light scattering at the interface top of the tear layer 102 and the air localizes these fringes. The spacing between these fringes depends on the physical characteristics of the thin film, such as the thickness, along with the angle of incidence and the angle of observation. There is at least one other mechanism producing interference: the scattering centers at tear film surface. These characteristics contribute to having an interference pattern with multiple origins. The sources of the interference pattern are very difficult to be picked up by simple observation. Through spatial autocorrelation analysis, however, these characteristics reveal themselves.

The spatial autocorrelation of an image described by the matrix I(x,y) is given by Equation 1 below:

$$G_s(\xi, \psi) = \frac{\langle I(x, y)I(x+\xi, y+\psi)\rangle_{x,y}}{\langle I(x, y)\rangle^2_{x,y}} - 1 \quad \text{(Eq. 1)}$$

where $\xi$ and $\Psi$ are the spatial increments in the x and y directions, respectively, and the angle bracket indicates average over all the spatial locations in both x and y directions. The spatial autocorrelation is performed on a 2-D camera image which contains interference patterns from different sources, along with other features such as dots and lines with various sizes and orientations. These features in the camera image are difficult to differentiate using the human eye alone. By transferring the data into frequency domain, these features are more distinguishable.

The mathematical operation of spatial autocorrelation works by shifting an image in both the x and y directions by one pixel and multiplying it by itself. This routine is performed for half the size of the image, since there is symmetry in the spatial autocorrelation image. This process is time consuming however, and could be numerically intensive. In order to expedite the spatial autocorrelation calculations, fast Fourier transformation is applied. To perform the spatial autocorrelation analysis with fast Fourier transformation, the raw camera image first undergoes a 2-D transformation. Then the complex conjugate of this image is calculated and multiplied by the original transformed image. This would produce a power spectrum. In order to better visualize the features in the frequency domain, the inverse of the power spectrum is calculated. This process is fast and robust. FIGS. 2A-2E illustrate a graphical representation of how fast Fourier transformation is performed on images and the resulting image appears.

The spatial correlation image (SCI) contains the average shapes and sizes of features of the image. For example, if the image (of an image frame) is made of randomly placed features, the spatial correlation image which represents the average shape and size is then equal to the weighted average of the shape and size of each individual feature. If the average image is made of circular and linear fringes, such as in an interference pattern, the SCI will represent the average periodic shape of the fringes. Specifically, the spatial correlation calculation only gives the average features of the image, disregarding their specific location in the image. The SCI is symmetric in the vertical and horizontal directions.

The real characteristics of the raw camera image, which are hidden from the eye, are apparent in the SCI, specifically in the background of the autocorrelation peak. It is important to distinguish between the spatial autocorrelation function of the camera image and the image itself, as they represent two different spaces.

The periodic pattern which is observed at the ocular surface originates from interference within the tear film 102 and from scattering at the surface of the tear film 102. This is important to understand as it causes different families of interference patterns to appear in the raw camera image. The scattering from the surface and the internal reflection within the tear film layers will give rise to fringes of equal inclination. FIG. 1B displays the physics behind the formation of the pattern that is observed in the raw camera image.

The spatial autocorrelation function and analysis processes, such as applying a high-pass filter, act as a filter to select the specific periodic patterns which correspond to the thickness of a thin film. For thicknesses of about 3 um and an incident angle of about 10 degrees, periodicities in the autocorrelation function extending about 6-7 pixels have been observed (1 pixel being 12 μm). In addition, the 2D pattern at the surface is not necessarily oriented along the camera axes. If one considers the x-y axis of the camera, the projection of the pattern will produce different spatial frequencies along the axes. Depending on the angle of the pattern, the period along one axis can be very long. The method disclosed herein calculates the true period, not just the projection on the camera axes.

In essence, the physical principle for the formation of the periodic pattern is the interference between two sets of waves. The fringes are localized at the tear surface layer, due to slight scattering of this surface. The reflection at the inner surface of the tear film 102 produces a slight rotation or displacement in 3D of the system of waves. A moiré type of interference visualizes the underlying microscopic pattern. Superimposed to this pattern, there are many features such as lines, and rings and other structures generated by scattering centers at the surface and, possibly the heterogeneity of the surface itself. As a consequence of the spatial features of the illumination pattern, scattering centers, and other imperfections, the pattern may be analyzed using the autocorrelation function and after selecting the correct periodic pattern. The periodic pattern is in general complex, although it follows the basic dependency on the tear film thickness. It has been found that the period of the pattern depends on the inverse of the thickness of the film.

The SCI is then fitted using a specific mathematical model. The model that will be discussed here is a function of size, shape and orientation of the particles in the laser speckle and interference pattern. Additionally, the model accounts for any other features such as lines or interference patterns in the images. This algorithm subtracts the overall spatial correlation (the two Gaussians) and then analyzes residuals (the smaller oscillations). If the residuals exhibit the large oscillations they will be removed through high-pass filtering.

The original camera image has dots and fringes in terms of lines along with circular interference patterns. This pattern arises from reflection of light from the tear film which self-interferes. The SCI has the same average features, but they are all located near the center of the image.

Therefore, a fitting algorithm to track the changes in these features in the SCI is utilized. This algorithm analyzes only the projections of the features on the vertical and horizontal axis of the SCI. With this method, the fitting routine becomes easy, robust and fast. In principle, the spatial autocorrelation function, using two Gaussian components and one term describing the interference pattern, could be fitted directly.

Figure 2A:
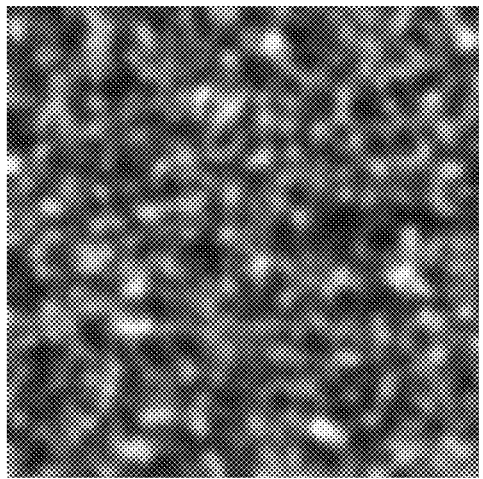
FIGS. 2A-2D illustrate a graphical representation of how fast Fourier transformation is performed on images and the resulting image appears.
Figure 2B:
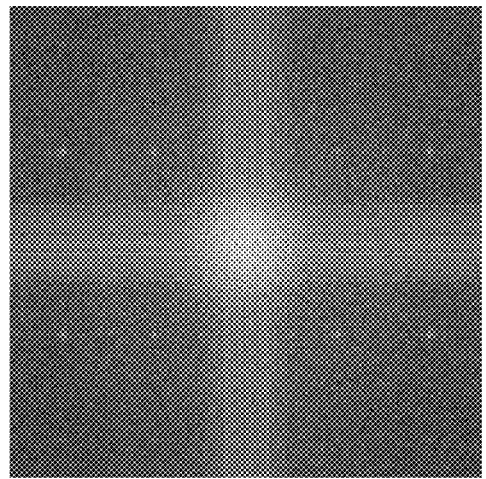
Figure 2C:
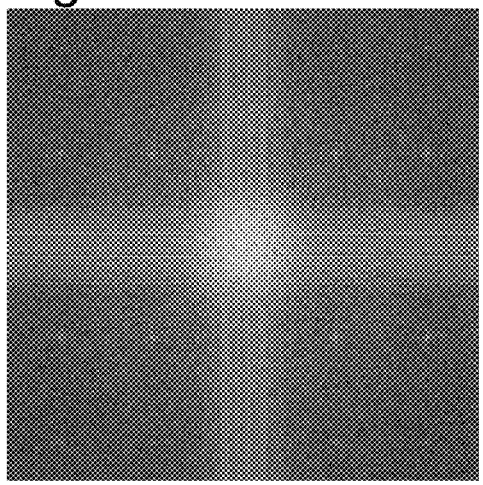
Figure 2D:
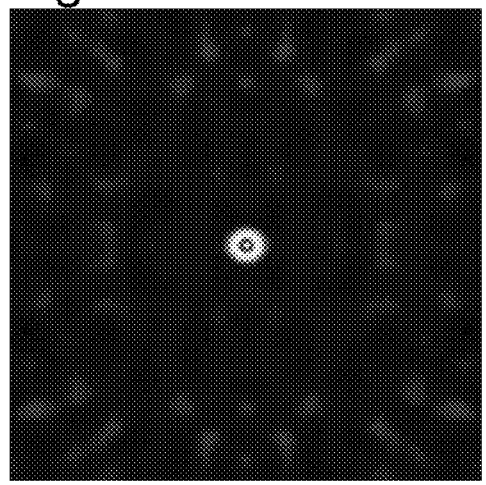
Figure 4A:
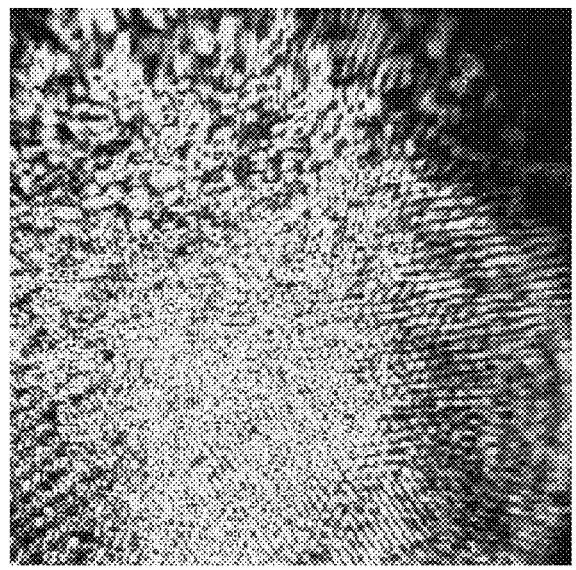
FIG. 4A illustrates a raw camera image having many features such as small and large dots with different orientations and interference fringes being observable.
Figure 4B:
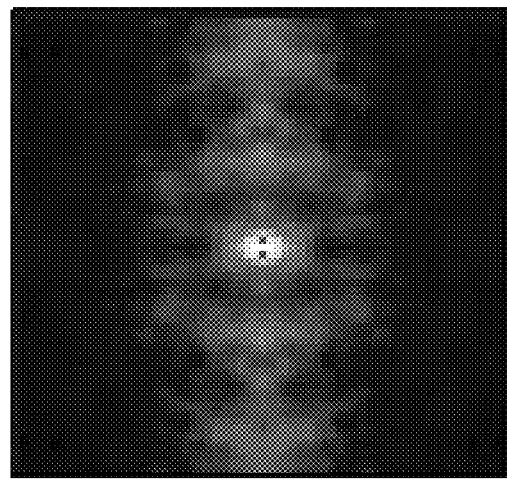
FIG. 4B illustrates the spatial autocorrelation image of FIG. 4A.

The laser diode illumination source 12 used in the experiments had a non-uniform illumination, producing an elongated pattern. A series of raw camera images are acquired (FIGS. 2A and 4A). For each frame the spatial correlation image was calculated and four consecutive frames were averaged. The SCI is displayed as illustrated in FIGS. 2B and 4B. Then the frame index is advanced by one, and the calculation is repeated. In the next section it is described how the thickness information is derived from the changes in the sinusoidal background of the SCI.

A mathematical model has been developed to extract the thickness and spatial features of the tear film, based on the spatial correlation analysis. This model analyzes the sinusoidal background which is superimposed on the spatial correlation, and calculates the "interference term" which is directly related to the thickness of the tear film.

Figure 2E:
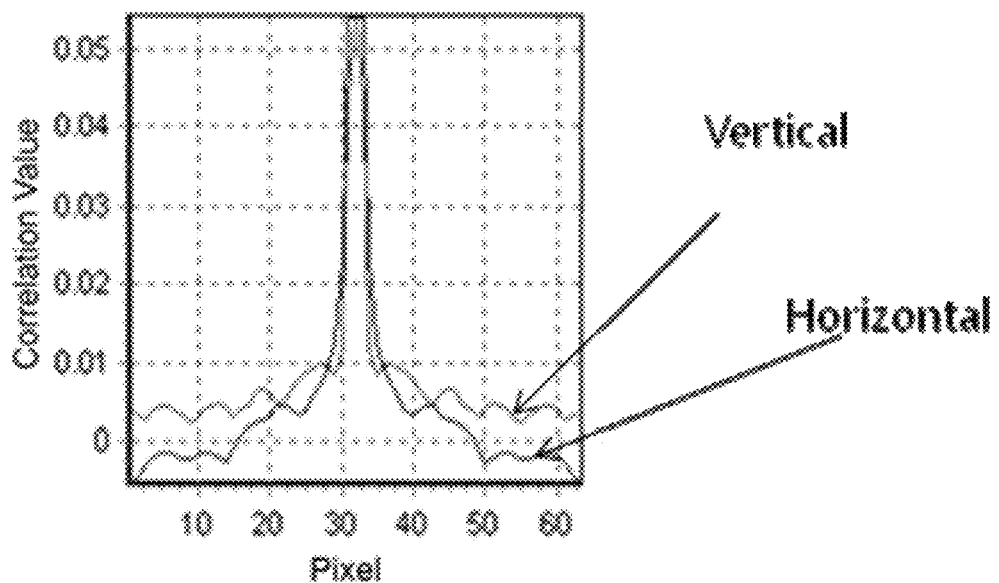
FIG. 2E illustrates the sinusoidal background of the SCI of FIG. 2B. The image contains the Gaussian terms along with the residues for both vertical and horizontal axis of two-dimensional image. The width of the pixels is illustrated on the x-axis while the correlation value (e.g., number of dots/average intensity of image) is on the y-axis.
Figure 2F:
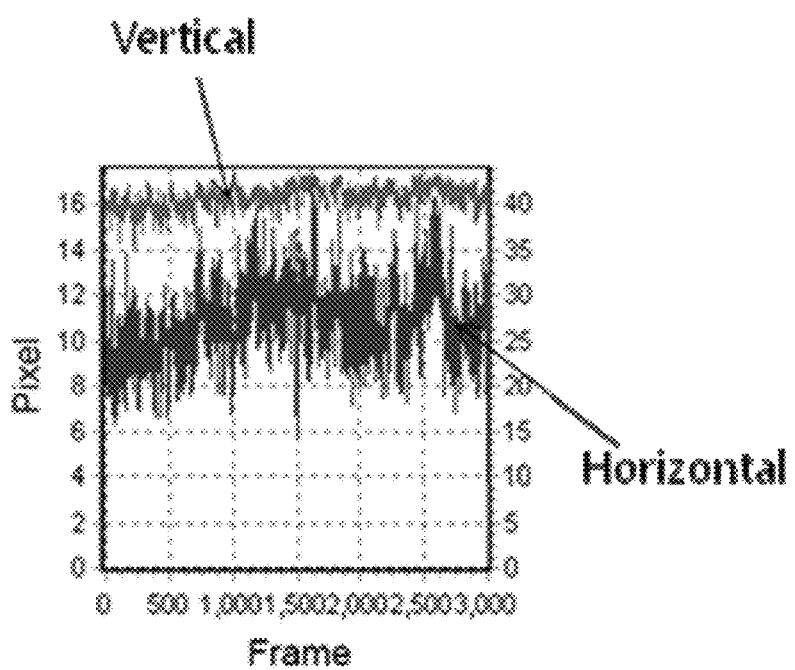
FIG. 2F illustrates the width of the SCI recorded over time. The vertical-labeled line represents the width in Y direction and the horizontal-labeled line represents the width in the X direction. Frame number is indicated on the x-axes which correlates with time. In this experiment, 3000 frames were acquired.
Figure 4C:
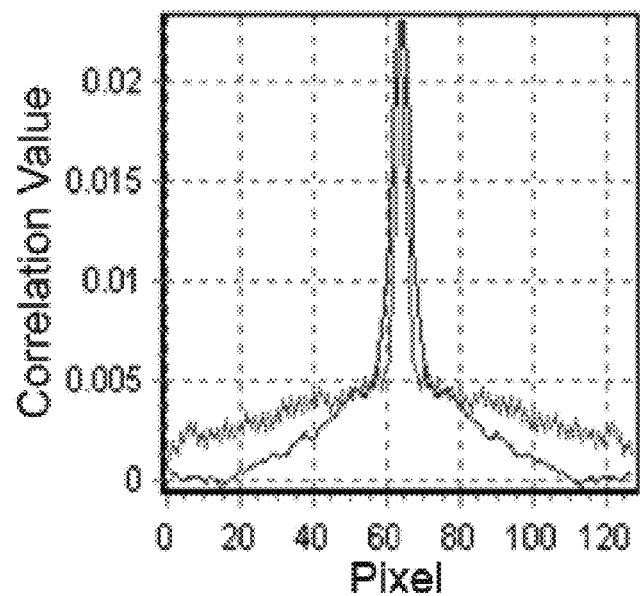
FIG. 4C illustrates the vertical and horizontal projections of the spatial autocorrelation image of FIG. 4B.

The sinusoidal background of the SCI is illustrated in FIGS. 2E and 4C in terms of correlation value vs. pixels. FIG. 2F illustrates the changes of the vertical components of FIG. 2E over a period of time (3000 frames). As seen in FIGS. 2E and 4C, the width of the pixels is illustrated on the x-axis while the correlation value (e.g., number of dots/average intensity of image) is located on the y-axis. The SCI embeds three major components in addition to the sinusoidal pattern due to the tear film interference: shape, size and orientation of features in the image. Since these features are in relatively large number, a Gaussian model is used to describe them. The first feature is the primary Gaussian (the large oscillation) and the second feature is the smaller sinusoidal oscillation. The period (frequency) of the interference caused by the tear film is extracted with this model and is used to calculate the overall thickness of tear film. The Gaussian terms and their residues are illustrated in FIGS. 2E and 4C for both the vertical and horizontal axis of the two-dimensional image. The sinusoidal background has two major components embedded in it. The first component is the primary Gaussian (the big oscillation) while the second is the smaller sinusoidal oscillation.

Figure 3:
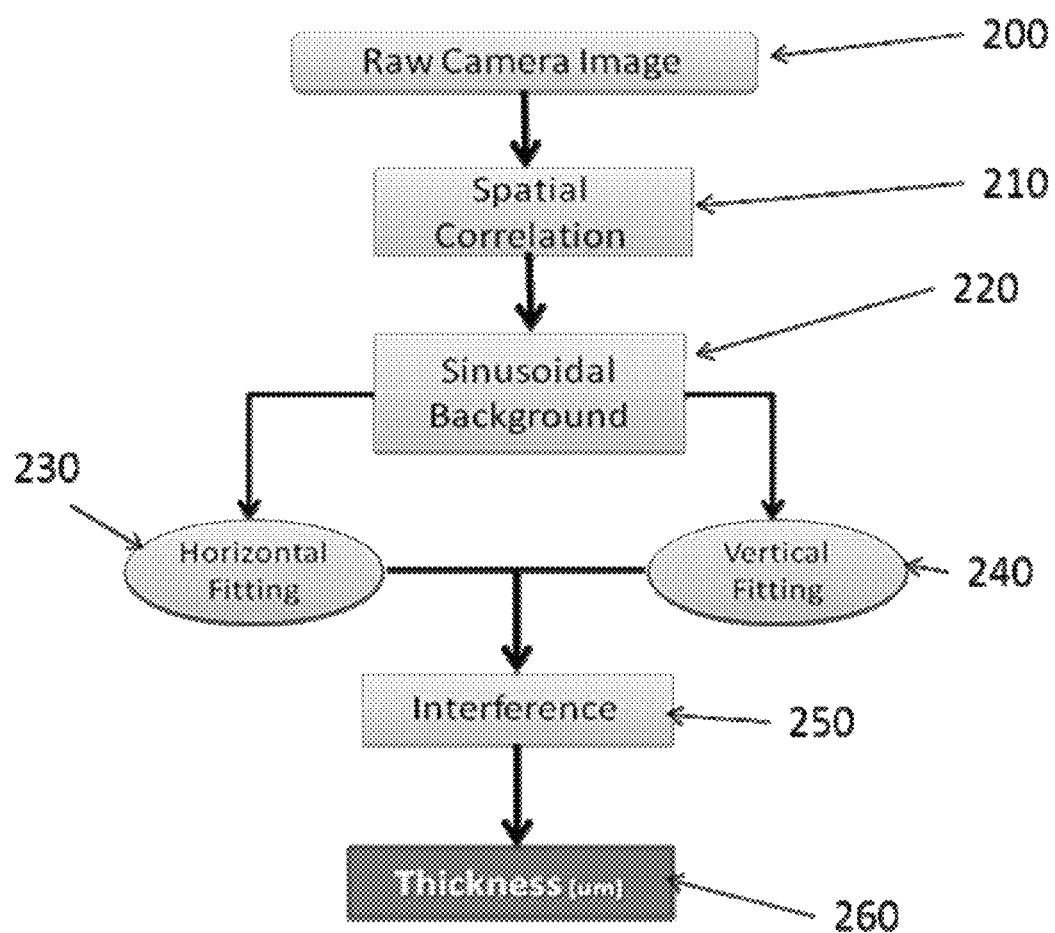
FIG. 3 is a flow chart illustrating the fitting algorithm used in connection with the method.

The algorithm of the model discussed herein is shown in FIG. 3. In this algorithm, the raw camera image is obtained in operation 200. The raw camera image may comprise a single frame or multiple frames. The SCI of the frame (or frames) is then obtained in operation 210. Next, as seen in operation 220, the overall spatial correlation (the primary Gaussian) is subtracted and then the residues (the smaller oscillations) are analyzed. Once the primary Gaussian is subtracted leaving the residues, the vertical and horizontal projections of the SCI is then subject to a curve fitting algorithm as illustrated in operations 230, 240.

As previously mentioned, if the original camera image has dots and lines (FIG. 4A), the spatial correlation image has also the same average features but all located to the center of the image (FIG. 4B). The interference caused by the layers of tear film is extracted with this model and is used to calculate the overall thickness of tear film. Due to high variability of the location where these features appear in the original camera image, it is very difficult to model their behavior in the raw image. Instead using the SCI image, all the various features appear in this image independently of their location and they are easy to distinguish. Therefore, a fitting algorithm was developed to track the changes in these features in the SCI by analyzing only their projections on the vertical and horizontal axis of the SCI as illustrated in operations 230, 240. FIG. 4C illustrates the vertical and horizontal projections of the SCI. With this method, the fitting routine became easy and robust and produced reproducible results.

Figure 4D:
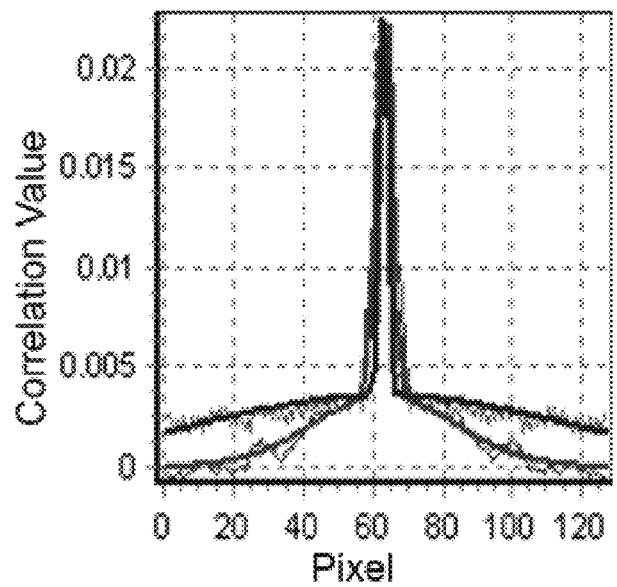
FIG. 4D illustrates the primary Gaussian fit in the spatial autocorrelation image of FIG. 4C.
Figure 4E:
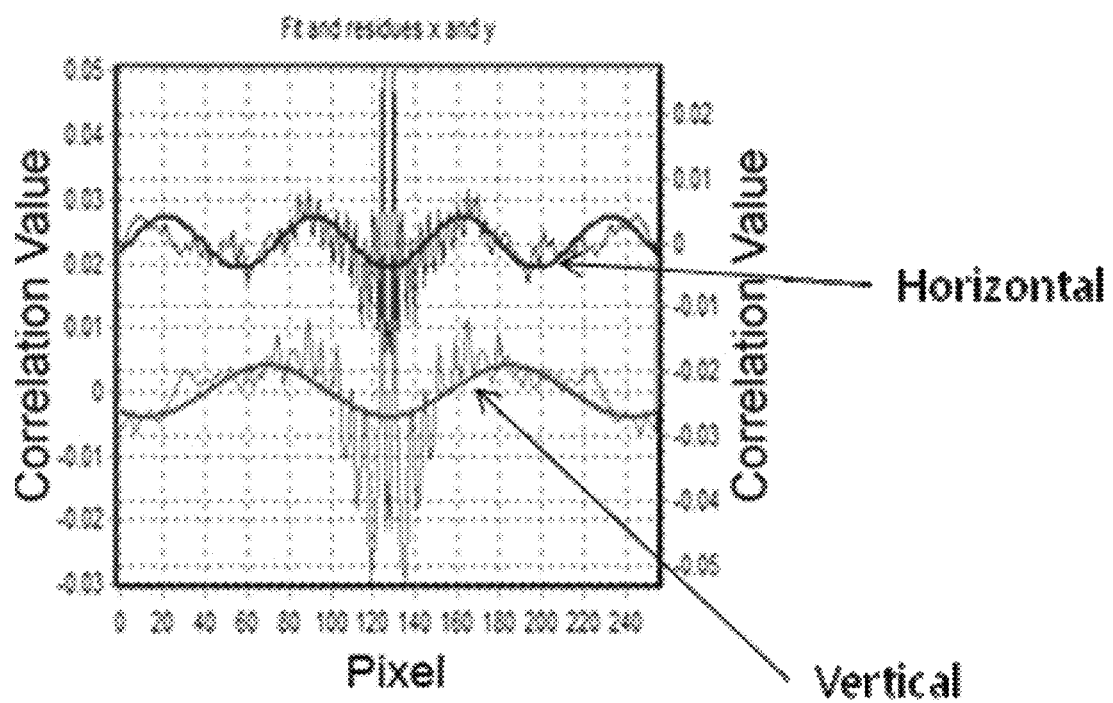
FIG. 4E illustrates the vertical and horizontal fitting of the sinusoidal residuals after removal of the Gaussian components.

As described herein, the SCI is obtained in operation 210 from the camera images. The fitting algorithm fits the SCI function which is modeled as the sum of the two Gaussians (different in the in the vertical and horizontal directions). This fit of the average dots (small and large) is subtracted from the SCI. The residues show the periodic oscillation due to the interference fringes. The process of calculating the SCI from the raw camera image, filtering the primary Gaussians, and fitting the residuals after high-pass filtering is done on the first frame of the image-stack. This is called initialization. This initialization of the fit is needed to start the scanning of all the frames with reasonable starting values (trying to minimize Chi-Square values). Then the fitting algorithm only slightly changes the values of the parameters to accommodate the changes that occur from frame to frame. The model tracks the changes in the sinusoidal background of the SCI once the primary Gaussians representing the small and large image features are removed from it (FIG. 4D). The routine for extracting the thickness of the tear film works on the differential of the SCI only (FIG. 4E).

The specific relationship we use for the first fit for the horizontal projection of the SCI is given by:

$$H = B + G_{1x}e^{\frac{-(x-C)^2}{2\sigma_{1x}^2}} + G_{2x}e^{\frac{-(y-C)^2}{2\sigma_{2x}^2}} \quad \text{(Eq. 2)}$$

Where B is the overall background, $G_{1x}$ and $G_{2x}$ are two Gaussian terms in the x direction, C is the center point of the image where the Gaussian fitting is started, which is the center of the SCI image, $\sigma_{1x}$ and $\sigma_{2x}$ are the standard deviations in the "x" direction corresponding to the first and second Gaussian functions in (Eq. 3).

Accordingly, the relationship for the vertical fit is given by:

$$V = B + G_{1y}e^{\frac{-(x-C)^2}{2\sigma_{1y}^2}} + G_{2y}e^{\frac{-(y-C)^2}{2\sigma_{2y}^2}} \quad \text{(Eq. 3)}$$

Where B is the overall background, $G_{1y}$ and $G_{2y}$ are two Gaussian terms in the y direction, C is the center point of the image which is known. The vertical and horizontal fits are shown in FIG. 4E.

The results of this fit using the two Gaussians is then subtracted from the SCI and the residues are now fitted with a periodic function that we associate to the interference term. The interference (I) term is given by:

$$I = A(1 - \cos(k_x x) - \cos(k_y y)) \quad \text{(Eq. 4)}$$

Where I is the interference, A is the amplitude, and $k_x$ and $k_y$ are the projections in the x and the y directions of the interference pattern. All units in the above relationships are in terms of the number of pixels in the autocorrelation function. X and Y are shifts expressed in terms of number of pixels and $k_x$ and $k_y$ are in unit of inverse number of pixels needed for one period of the interference pattern. The operation of obtaining the interference (I) is illustrated by operation 250 in FIG. 3.

$K_x$ and $K_y$ are given by:

$$k_x = P\cos(\phi) \quad \text{(Eq. 5)}$$

$$k_y = P\sin(\phi) \quad \text{(Eq. 6)}$$

Where P is $2\pi$ in units of 1/pixels of the interference pattern in the autocorrelation function and $\phi$ is the angle of the pattern with respect to the x and y axis. Since the pixel size (in terms of micrometer) of the camera and the optical magnification are known, the period of interference (P) could be calibrated.

The thickness t then can be calculated by:

$$t = \frac{\lambda}{nP\sin(\theta)} \frac{\cos(\beta)}{\cos(\theta)} \quad \text{(Eq. 7)}$$

where $\lambda$ is the wavelength of the monochromatic light source in units of μm/pixels, n is the refractive index of the medium which is assumed to be water, and $\theta$ is the incident angle and $\beta$ is the refraction angle. The operation of obtaining the thickness (t) is illustrated by operation 260 in FIG. 3.

Equation 7 was calibrated with a series of films of known thicknesses. The pattern of luminous and dark regions at the surface of the tear film 102 forms due to interference between two sets of waves. One set is caused by the incident light, while the second set is the waves refracted, and then reflected, by the tear film-cornea interface. These two sets of waves form stationary nodes because of the constant phase difference which is caused by reflection at the inner tear film surface. These two set of waves interfere at the surface. In the case of the eye 100, fringes are localized at the surface, because of the slight scattering at the outer surface of the tear film 102. There is slight displacement and change of orientation (in 3D) of the reflected set of waves with respect to the incident set, which is proportional to the film thickness. Due to this change of orientation, there is a moiré kind of interference that forms at the surface. In moiré interference, patterns are obtained by combining intensities, while in optical interference; patterns are obtained by combining electric fields. The period of this pattern depends on the inverse of the thickness, since the change of orientation/displacement depends on the optical path in the film. Since the pattern is localized at the surface, it can be observed independently of the numerical aperture of the detection system. Given the complexity pattern formation, the factor K in equation 7 was calibrated for the geometry of the set-up described herein and, therefore, the equation for the thickness takes on the following form:

$$t = \frac{K}{P} \tag{Eq. 8}$$

Equation 8 shows the relationship between the thickness of the pre-corneal tear film thickness and the period of the interference from the moiré-like pattern which is observed in the raw camera image. K is simply a constant representing the terms which were described in equation 7.

Experimental Results

Experiments were performed on a live rabbit model. The rabbits were provided by and imaged at the University of California, Irvine, Medical Center and approved protocol (IRB# 2004-2550) for these experiments. Rabbits were sedated at the time of the measurement. Each rabbit was placed in a container with the eyes held open by speculum. The laser beam, described above, was pointed at an angle toward the eye 100 of the rabbit and focused thereon. It is not necessary to point to the center of the eye with the laser beam. This is one characteristic of the system 10 and method that makes the alignment extremely easy. The camera 16 was placed about 2.67" inches away from the surface of the eye 100. This was the focal length of the 1X microscope objective lens 18 used in the experiments. The detector camera 16 in the imaging system 10 picks up the speckle on the eye 100 along with any interference pattern. The exposure time was set to 1 ms enabling image capture at a high frame-rate of about 300 frames per second. For each experiment two to three thousand frames were acquired. Therefore, the data acquisition time ranged from 6 to 9 seconds. The raw camera movies were then streamed to a computer 20 and saved as a raw file for further computational analysis.

Figure 5:
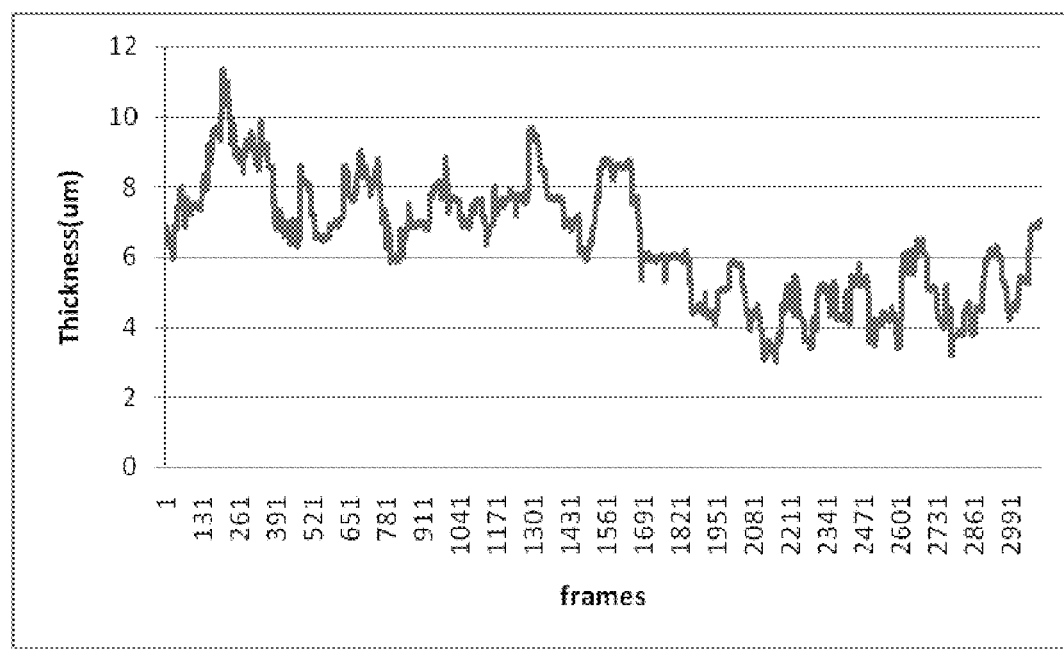
FIG. 5 illustrates the baseline thickness of a rabbit's tear film layer over approximately ten seconds.

In FIG. 5, the baseline thickness recovered from the analysis algorithm is illustrated. The baseline thickness is the measurement without the addition of any solutions to the eye 100. In this experiment, the rabbit's eye 100 was held open for about 2 minutes before starting the experiment. The overall thickness is displayed over time. The thinning of the tear film was observed over this period of time. Because the measurement is continuous, we can reveal the changes of thickness of the tear film as a function of time with significant resolution. There are apparent periodic changes in the film thickness with a period of about 0.83 s (every 250 frames). In this experiment the average thickness value was calculated to be 6.45 μm. Other observations indicated tear film thicknesses of approximately 10 um. These measurements are consistent with measurements of tear film thickness obtained by others. See e.g., S. Mishima et al., *Some Physiological Aspects of the Precorneal Tear Film*, Arch Opthalmol 73(2), 233-241 (1965); Prydal et al., *Study of precorneal tear film thickness and structure by interferometry and confocal microscopy*, Invest. Opthalmol. Vis. Sci. 33(6), 1996-2005 (1992).

Figure 6:
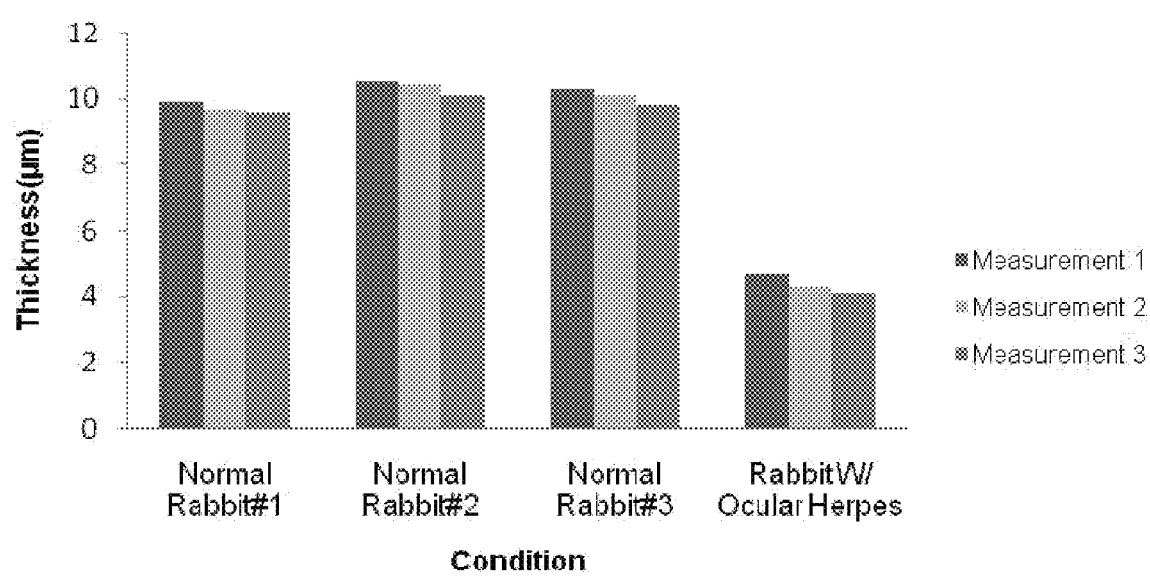
FIG. 6 illustrates the overall data for the 4 rabbits involved in this study. Three rabbits in this work exhibited tear film thickness of approximately 10 µm. One rabbit with ocular herpes had an ocular tear film thickness of approximately 4.5 µm.

FIG. 6 illustrates the data obtained from four rabbits involved in the FASIC study. In particular, the graph displays the overall data for the 4 rabbits involved in this study. Three "normal" rabbits in this experiment exhibited tear film thickness of approximately 10 μm. One rabbit with ocular herpes had an ocular tear film thickness of approximately 4.5 μm. Three such measurements were made for each rabbit as illustrated in FIG. 6.

Figure 7:
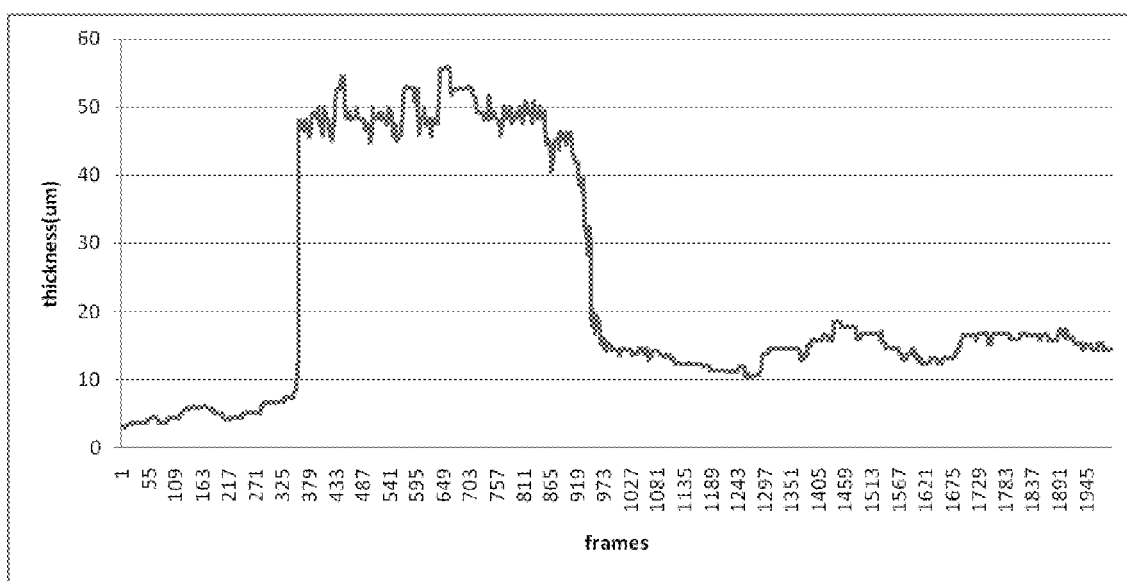
FIG. 7 illustrates the changes in the thickness of a rabbit's tear film after instillation of Refresh Tear Plus® solution after starting with a dried-out rabbit eye. The thickness of the tear film increases approximately ten fold. After another two seconds (when the bulk of the drop is out of the imaging plane), the tear film starts finding a stability in thickness. At this point, the thickness stays at approximately 12 µm (consistent with the value that was observed in the previous experiment), and holds this thickness throughout the data acquisition.

FIG. 7 demonstrates the continuous monitoring of the tear thickness. In this experiment, the rabbit started off with a dry eye. Initially the thickness was found to be approximately 5 μm. One and a half (1.5) seconds into the measurement, at frame 350, a drop of Refresh Tears Plus® eye lubricant was instilled onto the eye. A 10-fold increase in thickness is observed in the tear film, peaking at about 50 μm. The tear stays thick for about two seconds, which is the time required for the drop to travel through the imaging plane. After the drop expands and the product starts to distribute more uniformly, the tear film maintains a stable thickness of approximately 12 μm throughout the measurement. This value is correlated to the other experiments conducted with Refresh Tears Plus® eye lubricant drops.

Figure 10:
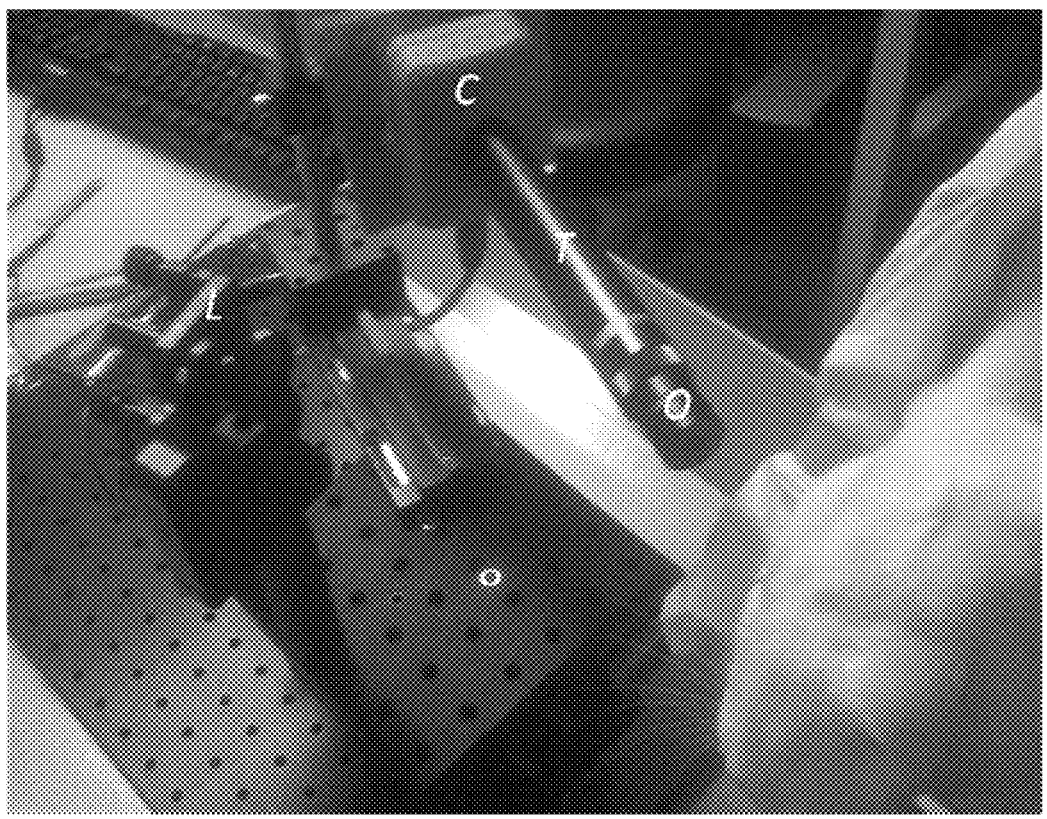
FIG. 10 is a photograph of the experimental setup showing the basic components needed for the FASIC method. Monochromatic light source is illuminated from the 635 nm laser (L) onto the rabbit's inferior cornea. The cMOS camera (C) that is connected to the objective lens (O) through an extender tube (T) picks up the interference pattern along with the laser speckle on the ocular surface.

Experiments were also conducted in a human pilot study. FIG. 10 illustrates a photographic image of the experimental setup. Monochromatic light source is illuminated from the 635 nm laser (L) onto the rabbit's inferior cornea. The cMOS camera (C) that is connected to the objective lens (O) through an extender tube (T) picks up the interference pattern along with the laser speckle on the ocular surface. In particular, the pre-corneal tear film thickness of forty individuals was measured. Tear film thickness was measured in twenty-two subjects with dry eye and in eighteen with normal eyes. Retention time of a topical eye-drop was studied on twenty subjects with dry eye. All subjects enrolled in the study were advised not to use topical eye-drops on the two days prior to each thickness determination (initial and repeatability visit), and contact lens wearers agreed to discontinue lens wear and topical eye-drops for two days prior to thickness determinations. With the exception of the prohibition of pre-visit topical eyedrops, the subjects were assessed concurrent with existing dry eye management. This might include use of systemic tetracycline derivatives or supplements such as omega 3 fatty acids.

After the initial visit to determine eligibility, the visual acuity of each enrolled subject was first examined. The biomicroscopy, with minimal adnexa manipulation was then verified. Subjects were directed to another room where the FASIC setup was located. Depending on which eye was the study on, the FASIC setup was aligned. The focus of the camera assembly was verified to be consistent amongst all the subjects. 1000 frames were collected for each subject. Only 500 frames of which were analyzed in order to be under the inter-blink intervals. After the measurements, subjects were examined with sodium fluorescein dye (2.0 μl of 1.0% non-preserved sodium fluorescein) to monitor for corneal disruption. Another appointment was set up for the next visit within 7±2 days within the same one-half day (i.e., either in AM or PM as at initial tear thickness measurement visit). During the follow-up visit, the same sequence of tests was performed, except that no sodium fluorescein dye examination was performed.

The normal and dry eye tear thickness data were compared using 2-sample t-tests at both visits. Intraclass correlation was used to examine repeatability. Correlational analysis of thickness relative to both Schein symptom scores (0-24 scale) and total corneal staining (0-20 scale) was undertaken. Preliminary tear thickness sensitivity and specificity analysis was undertaken using a receiver operating characteristic (ROC) approach. A general linear mixed model was used to compare the tear thickness over time for the retention of effect experiment at Visit 2. Dunnetts Simultaneous Tests (corrects for multiple comparisons) were used to determine significant differences from the baseline, pre-instillation tear thickness. Multiple linear regression analysis was used to examine the effect of factors such as age, contact lens wear and sex on tear thickness.

The subject demographics for this study sample are summarized in Table 1. Forty subjects completed both visits, 22 dry eye subjects and 18 without dry eye. Of these, there were 19 males and 21 females, with more females in the dry group and all six of the soft lens wearers in the dry eye group. Overall, the ethnic groups represented are representative of the local population.

TABLE 1

Sample demographics

|  | Age | Sex | | Ethnicity | | | |
|---|---|---|---|---|---|---|---|
|  |  | Male | Female | Caucasian | Asian | Hispanic | African American |
| Normals* | | | | | | | |
| Median | 26.5 | 12 | 6 | 9 | 2 | 3 | 1 |
| Mean | 29.0 | | | | | | |
| SD | 8.3 | | | | | | |
| Drys | | | | | | | |
| Median | 32.0 | 7 | 15 | 10 | 5 | 5 | 2 |
| Mean | 38.8 | | | | | | |
| SD | 13.8 | | | | | | |

*did not satisfy more than one of the dry criteria (i.e., symptoms >7/24, TBUT ≦7.0 seconds, or corneal staining ≧4.0 on a 0-20 scale)

Relative to safety and comfort, the procedure was well-tolerated in all subjects. There were no instances of visual acuity loss, visible corneal changes or adnexal irritation. There were no occurrences of excess (i.e., beyond that present at the eligibility visit) corneal staining in the area of thickness measurement (using 2.0 µl of 1.0% NaFI, 10 minutes post-FASIC measurement).

It was first considered whether the tear film thickness values were different for subjects with normal eyes compared to the dry eye group at visits 1 and 2. For the first visit, the values obtained with the FASIC method averaged 3.05±0.21 µm and 2.48±0.27 µm for normals (n=18) and dry eye subjects (n=22), respectively. These thicknesses were statistically significantly different (two-sample t-test, p<0.001).

Figure 8:
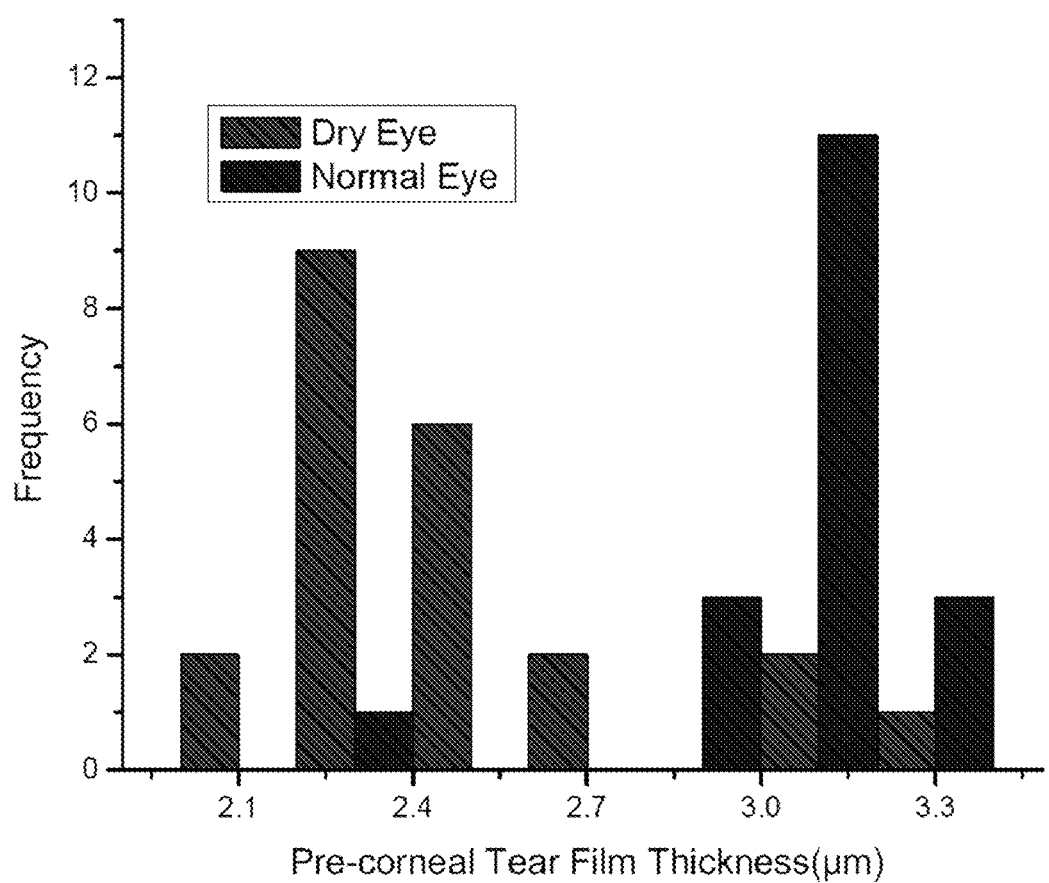
FIG. 8 illustrates a histogram of individual data points obtained in the human study.

At the second (repeatability) visit, mean tear thickness values were 3.06±0.18 µm and 2.46±0.25 µm for normals (n=18) and dry eye subjects (n=22), respectively, and were also statistically significantly different (two-sample t-test, p <0.001). FIG. 8 shows the histogram of the individual data points obtained with the FASIC measurement. This figure displays the individual measurements on forty subjects. Aside from the outliers in each group, the data set is suggesting a bi-modality of the data. The majority of the data points are located at the two ends of the spectrum and there is a gap in the middle.

Figure 9:
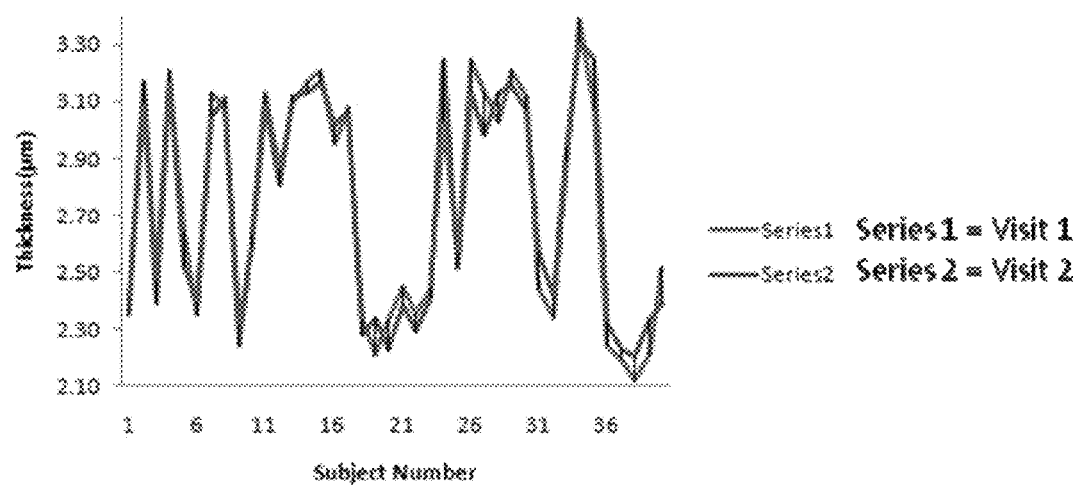
FIG. 9 displays the relative correlation between the data from the two FASIC visits in the human study.

The repeatability of the thickness values in normal and dry eye subjects in visit 1 to 2 was evaluated by intraclass correlation coefficient (ICC). ICC values of 0.935 and 0.950 were obtained for the normal and dry eye groups, respectively. These are extremely high values and demonstrate good repeatability of the FASIC thickness measurement. FIG. 9 displays the relative correlation between the data from the two FASIC visits.

The mean values found for non-dry eye subjects were approximately 3.1±0.2 µm for both visits (n=18). These are in good agreement with the data of others who found a mean value of approximately 3.0 µm in normal humans, also using a direct, non-invasive method. Moreover, at both visits we found a highly statistically significant tear thickness difference (p<0.001 at visit 1 and 2) for dry eye subjects (~2.5 µm, n=22) compared to non-dry eye individuals. For both non-dry eye subjects and dry eye subjects, the short-term (within one week) repeatability was excellent (ICC of 0.94 and 0.95, respectively).

The system and method described herein provides a useful technique for imaging the ocular surface to obtain highly repeatable and accurate measurements of tear film thickness. The results indicate that spatial correlation analysis is a quick and robust method for obtaining the depth profile of very thin biological films that exhibit interference upon light illumination. The thickness of tear film was measured in the live rabbit model eye under different conditions and quantified in response to different artificial tear solutions. Measurements revealed the details of the changes of thickness as a function of time.

By analyzing the spatial fluctuation of laser speckle and interference pattern from a series of images using the SCI one can extract the depth profile using a model to describe the various components of the SCI. In particular the component associated with the interference pattern arises from the tear film layers. The specific system used for the measurement is robust, inexpensive, easy to align, portable and non-invasive. The system is compatible with the common opthalmological instrument used to look at fungus or to measure eye curvature. This technique has great potential for commercialization and clinical applications, given its unique qualities of portability and cost-effectiveness. The system components requirements are extremely modest.

The approach described herein is applicable to any biomedical imaging system that exhibits interference in a thin film. FASIC can provide ophthalmologists or others with means to monitor the pre-corneal tear film thickness non-invasively in real-time. The technique can also be used to characterize the components of the tear film such as the lipid layer. FASIC can also characterize the behavior of the tear film over time, such as the thinning-out phenomena. The methods and devices may also be used to provide a surface map of the eye. Additionally, this technique can assist companies that make contact lenses, contact lens solutions, and artificial tear solutions to conduct in-house testing to examine the effect of their products on tear film thickness.

The FASIC technique may also be used with various alternative light sources to obtain an interference pattern. The interference pattern would come from the layers of the tear film. For example, two or more lasers may be used with each laser having a different wavelength. Multiple wavelengths would provide information on the components of the tear film.

While embodiments of the present invention have been shown and described, various modifications may be made without departing from the scope of the present invention. The invention, therefore, should not be limited, except to the following claims, and their equivalents.

What is claimed is:

1. A method of determining the thickness of an ocular tear film of a subject comprising:
   irradiating an eye with a light source;
   capturing a speckle and/or interference pattern produced by the irradiated eye with a camera, the camera capturing said speckle and/or interference patterns in a plurality of frames;
   calculating a spatial autocorrelation of the raw camera image for the plurality of frames;
   removing the primary Gaussian component from the autospatial correlation so as leave sinusoidal residues;
   subjecting the sinusoidal residues to horizontal and vertical fitting with a periodic function, the periodic function associated with an interference term; and determining the thickness based at least in part on the interference term.

2. The method of claim 1, wherein the light source comprises a laser light source.

3. The method of claim 1, wherein the light source comprises a plurality of lasers having different wavelengths.

4. The method of claim 1, wherein the light source comprises a non-coherent LED light source and the capturing operation comprises capturing an interference pattern.

5. The method of claim 1, wherein the light source comprises a broadband light source and at least one filter interposed between the light source and the eye.

6. The method of claim 5, further comprising tuning the at least one filter.

7. The method of claim 1, where the speckle and/or interference pattern is captured with a CMOS or CCD camera.

8. The method of claim 1, wherein the spatial autocorrelation is determined based on an average of a plurality of frames.

9. The method of claim 1, wherein the spatial autocorrelation of the speckle and/or interference pattern for the plurality of frames is calculated with a computer operatively connected to the camera.

10. A system for determining the thickness of an ocular tear film of a subject comprising:
    a source of coherent radiation;
    a camera configured to capture a speckle and/or interference pattern produced by the irradiated eye in a plurality of frames;
    at least one microprocessor configured to calculate a spatial autocorrelation of the speckle and/or interference pattern for the plurality of frames, the at least one microprocessor further configured to remove the primary Gaussian component from the spatial autocorrelation so as leave sinusoidal residues and subjecting the sinusoidal residues to horizontal and vertical fitting with a periodic function, the periodic function associated with an interference term, the at least one microprocessor further configured for determining the thickness based at least in part on the interference term.

11. The system of claim 10, wherein the source of coherent radiation comprises a laser light source.

12. The system of claim 10, further comprising a filter configured to pass a filtered wavelength of coherent radiation.

13. The system of claim 12, wherein the filter is tunable.

14. The system of claim 10, wherein the camera comprises a CMOS or CCD camera.

15. The system of claim 10, wherein the at least one microprocessor comprises a computer operatively connected to the camera.

16. A method of non-invasively monitoring an ocular tear film thickness comprising:
    irradiating an eye with a light source;
    capturing a speckle and/or interference pattern produced by the irradiated eye with a camera, the camera capturing said speckle and/or interference patterns in a plurality of frames;
    obtaining a spatial autocorrelation of the raw camera image for the plurality of frames;
    extracting a sinusoidal background from the spatial autocorrelation;
    matching the sinusoidal background with a periodic function; and
    determining the thickness based at least in part on the periodicity of the periodic function.

17. The method of claim 16, wherein the thickness is repeatedly determined over a period of time.

18. The method of claim 17, further comprising placing an agent in the eye and monitoring the thickness over a period of time.

19. The method of claim 17, further comprising sequentially placing different agents in the eye and monitoring the thickness over a period of time.

20. The method of claim 19, wherein a favored agent is selected from the plurality based at least in part on the monitored thickness.

* * * * *